United States Patent [19]

Bauman

[11] 4,272,413

[45] Jun. 9, 1981

[54] DIALKYLUREA TEXTILE SOFTENING AND ANTISTATIC AGENTS

[75] Inventor: Robert A. Bauman, New Brunswick, N.J.

[73] Assignee: Colgate-Palmolive Company

[21] Appl. No.: 97,579

[22] Filed: Nov. 26, 1979

[51] Int. Cl.[3] .................... C11D 1/50; D06M 13/40; C07C 127/15

[52] U.S. Cl. .................... 252/525; 252/8.8; 252/544; 564/58

[58] Field of Search .................... 260/553 R; 252/544, 252/8.8, 525

[56] References Cited

U.S. PATENT DOCUMENTS

| | | | |
|---|---|---|---|
| 2,477,872 | 8/1949 | Haury | 260/553 R |
| 2,547,728 | 4/1951 | Abrams | 260/553 R X |
| 2,708,183 | 5/1955 | Ross | 252/544 X |
| 3,190,763 | 6/1965 | Schleede et al. | 260/553 R X |
| 3,691,082 | 9/1972 | Stimberg et al. | 252/542 X |
| 3,814,705 | 6/1974 | Inamorato et al. | 252/544 X |
| 3,862,905 | 1/1975 | Eckert | 252/544 X |
| 3,965,015 | 6/1976 | Bauman | 260/553 R X |
| 4,025,444 | 5/1977 | Murphy et al. | 252/8.8 |

*Primary Examiner*—Harris A. Pitlick
*Attorney, Agent, or Firm*—Norman Blumenkopf; Herbert S. Sylvester; Murray M. Grill

[57] ABSTRACT

Short chain carbamoyl derivatives of long chain aliphatic amines, wherein the amino nitrogen is attached to a non-terminal methylene group, useful as non-yellowing softening and antistatic agents for laundered fabrics, detergent compositions containing an effective softening and antistatic amount of said carbamoyl derivative and a method of softening and protecting fabrics against acquiring static electricity by contacting fabrics with said composition during laundering. These compounds provide softening and antistatic protection without reducing optical brightener performance and detergency performance of the detergent composition.

18 Claims, No Drawings

DIALKYLUREA TEXTILE SOFTENING AND ANTISTATIC AGENTS

This invention relates to novel softening and antistatic agents and detergent compositions to be used in the laundering of fabrics containing said softening and antistatic agent which is a disubstituted urea having the formula:

RNHCONHR' wherein R is a short alkyl group of 1-6 carbons, and R' is a secondary aliphatic hydrocarbon chain of 8-22 carbons.

DESCRIPTION OF THE PRIOR ART

The use of various and diverse chemical materials and particularly cationic quaternary ammonium compounds as softeners and antistatic agents for textile products is very well known in the art. It is also well known to employ such materials for their antistatic and softening effects during the laundering operation and particularly in the rinse cycle of the laundering process. This technique has been necessitated by the fact that the aforesaid quaternary compounds heretofore employed, being mainly cationic in nature, were not compatible with the anionic detergents, one of the major types of detergents used in the washing cycle.

It is also well known that there is a tendency for laundered articles to yellow or discolor when treated with aforesaid quaternary compounds.

Another disadvantage associated with the use of said cationic agents in the laundering of fabrics therewith is its interference with the deposition on the fabrics of optical brightener, thereby reducing optical brightener performance of a detergent composition containing said optical brightener.

Still another disadvantage of the cationic quaternary ammonium antistatic softener is its interference with the cleaning properties of the detergent by reducing the soil removal effected by the detergent, resulting in decreased washing effectiveness. The presence of the anionic detergent material substantially negates the fabric softening properties of the cationic quaternary ammonium compounds as well as counteracts the antistatic activity possessed by said quaternary compounds.

Accordingly, substituted urea compounds such as methylol urea has been found useful in the treatment of fabrics such as in textile finishing compositions, as disclosed in U.S. Pat. No. 3,651,139 to Feinauer et al; and N-octadecyl-urea formaldehyde has utility as textile softening agents as disclosed in U.S. Pat. No. 3,671,308 to Diery et al.

Similarly, substituted urea compounds have been used in the treatment of textile materials to provide a permanent softening effect as disclosed in U.S. Pat. No. 2,304,113 to Morgan et al; and fabric softener compositions containing diphenyl urea derivatives as stabilizers for quaternary ammonium fabric softeners is disclosed in U.S. Pat. No. 3,216,944 to Fredrickson, and the reaction product of urea with a cationic-containing compound such as a quaternary ammonium compound, a primary, secondary, or tertiary amine having at least one long alkyl chain, is disclosed in U.S. Pat. No. 3,256,180 to Weiss.

Urea, monobutyl urea, dibutyl urea, phenyl urea and acetyl methyl urea have been used in soap bars as disclosed in U.S. Pat. No. 2,374,187 to Flett; and substituted urea compounds with one or more alkyl groups containing 1-4 carbons have been used in hair preparations as disclosed in U.S. Pat. No. 3,149,042 to Habicht et al.

Low foaming cleaning compositions which may contain an alkylated urea substituted by two long alkyl chains, at least one on each N, which may be a straight-chain or branched is disclosed in U.S. Pat. No. 3,691,082 to Stimberg et al; and bleach-stable fabric detergent and/or softening compositions containing a substituted urea having the formula:

$RNHCONH(CH_2)_nNH_2$, wherein R is an alkyl group containing 2-18 carbons and n is 2-12 as the softening agent, is disclosed in U.S. Pat. No. 3,965,015 to Bauman.

Dialkyl urea compounds having a short alkyl group on one nitrogen and a long alkyl chain on the other nitrogen have been used in detergent compositions to enhance detergency and foaming as disclosed in U.S. Pat. No. 2,708,183 to Ross. U.S. Pat. No. 3,190,763 to Schleede et al also discloses disubstituted urea compounds such as N,N' dimethyl urea and N,N' didodecyl urea useful in the antistatic finishing of plastics.

However, none of aforesaid prior art substituted urea compounds or carbamoyl derivatives are short chain carbamoyl derivatives of long chain aliphatic amines, wherein the amino nitrogen is attached to a non-terminal methylene group; said compounds possessing both softening and antistatic properties.

SUMMARY OF INVENTION

It has now been discovered that the dialkyl urea compounds of this invention provide properties and fabric softening benefits, without causing fabric yellowing, do not interfere with optical brightener action and are compatible with detergents.

Accordingly, it is a primary object of the instant invention to protect fabrics against acquiring static-electrical charge during machine drying subsequent to the laundering.

Another object of the instant invention is to provide such protection in conjunction with conventional detergent compositions during the home laundering process.

A further object of the instant invention is to provide softening and antistatic protection without yellowing and without reducing optical brightener performance.

Still a further object of instant invention is to provide a softening and antistatic composition which may be employed in conjunction with detergents and other cleaning, brightening and laundering additives in a single step laundering operation.

Accordingly, the instant invention relates to softening and antistatic laundering compositions compatible with detergents; and to novel short chain carbamoyl derivatives of long chain aliphatic amines, where the amino nitrogen is attached to a non-terminal or internal methylene group, represented by the structural formula:

RNHCONHR', wherein R is a short alkyl chain containing 1-6 carbons, and R' is a secondary aliphatic hydrocarbon chain containing 8-22 carbons; and to the process for imparting softening and anti-static properties to fabrics which consists in treating fabrics with a composition containing a dialkyl urea substituted on one nitrogen by a secondary long chain aliphatic hydrocarbon and substituted on the other nitrogen by a short alkyl radical. More specifically, antistatic properties are imparted to fabrics by laundering the fabrics in a composition containing a detergent, preferably anionic or non-ionic, the above defined dialkyl urea compound and other ingredients such as phosphate or non-phosphate builders, optical brighteners, enzymes, bleaches, and other conventional additives.

The instant novel dialkyl urea compounds substituted on one nitrogen atom with a secondary long aliphatic chain containing 8–22 carbons and substituted on the other nitrogen with a short alkly radical containing 1–6 carbons and preferably 1–4 carbons, reduces or prevents the generation of static electricity on cotton and synthetic fabrics during laundering. These antistatic properties can be imparted to fabrics by laundering in a detergent composition containing said dialkyl urea compounds which are completely compatible with anionic, non-ionic, cationic and amphoteric detergents. This same treatment has been found to additionally confer a soft hand on cotton fabrics and to enhance the detergency action of the detergent composition. These beneficial effects are achieved without yellowing or discoloration of the fabrics and without interference with the action of optical brighteners that may be present in the detergent composition.

The dialkyl ureas may be single homologs or mixtures thereof. They may also be mixtures of isomers in which the RNHCONH-group is attached to any interior methylene group of the chain, with terminal substitution being precluded. Substitution may predominantly be at the more centrally located methylenes of the chain, at the central methylene, at the beta methylene, and so forth.

The dialkyl urea compounds of instant invention can generally be prepared by the conventional reaction of an amine with an isocyanate. For example, a solution of a long chain amine in methylene chloride may be treated with excess or equimolar quantities of a $C_1$–$C_6$ alkyl isocyanate. The product, isolated as a viscous oil or waxy solid, may be used as is or purified by distilling out low boiling fractions.

More specifically, instant novel dialkyl urea compounds are prepared from known starting materials by reacting an alkyl isocyanate such as methyl- or ethyl- or propyl- or butyl-isocyanate (RNCO) with a primary aliphatic amine containing 8–22 carbons wherein the amino functional group is attached to an interior carbon atom of the hydrocarbon chain. Beta amines, manufactured by the Armak Company, which are long chain primary amines, wherein the amino functional group is attached to an interior carbon atom, predominantly at the beta carbon atom, are suitable reactants. The reaction may be conducted at room temperature or under reflux conditions. Also, the reaction may be conducted in the presence of any non-reactive organic solvent such as methylene chloride, methyl or ethyl ether, benzene, chloroform or the like. The product is preferably isolated by evaporating in vacuum. The resultant dialkyl ureas which are usually made from mixtures of amines, are liquids, oils or solids.

The beta amines useful as a reactant herein may also be prepared by utilizing the Ritter reaction of converting α-olefins containing $C_8$–$C_{22}$ into internally substituted amines by reacting with sodium cyanide in the presence of a strong acid such as $H_2SO_4$, hydrolyzing the resultant formamide with hydrobromic acid into the beta amine, which is processed by neutralizing with sodium hydroxide, washing with water and $NaHCO_3$, drying over $Na_2SO_4$ and evaporating in vacuum and purifying by distillation.

The following examples illustrate the manner in which compounds of this invention are prepared, but is not limited thereto.

EXAMPLE 1

Preparation of the methyl carbamoyl derivative of the beta amine, $CH_3(CH_2)_{12-17}CH(CH_3)NH_2$ :

$CH_3(CH_2)_{12-17}—CH(CH_3)NHCONHCH_3$

To a solution of 165 g of said beta amine (Armeen L-15 from the Armak Company) in 500 methylene chloride heated on a steam bath to a reflux temperature, was slowly added from a dropping funnel, 36 ml isocyanate in 70 ml methylene chloride. The temperature was maintained at a gentle reflux during said addition which took 55 minutes. The mixture was refluxed for an additional hour and evaporated in vacuum to 179 g of a dark yellow oil.

EXAMPLE 2

Preparation of the methyl carbamoyl derivative of the beta amine, $CH_3(CH_2)_{8-11}CH(CH_3)NH_2$ :

$CH_3(CH_2)_{8-11}CH(CH_3)NHCONHCH_3$

To a solution of 112 g (0.5 mole) of above beta amine (Armeen L-11 from the Armak Company) in 300 ml methylene chloride heated to a reflux temperature was slowly added with gentle reflux 35 ml (0.6 mole) methyl isocyanate. Addition took one hour. The reaction mixture was refluxed for one hour longer, then evaporated in vacuum. After distilling out 10 g low boiling material at 70°–100° C., 121 g topped oil was recovered (purified).

The process described in the above examples may be varied by using other non-reactive organic solvents such as ether, benzene, chloroform, etc..

EXAMPLE 3

Preparation of methyl carbamoyl derivative of beta dodecylamine:

$C_{10}H_{21}CH(CH_3)NHCONHCH_3$

N-beta dodecyl-N'-methylurea 32 g (0.166 mole) beta dodecylamine in 60 ml methylene chloride was heated to reflux on the portable steam bath and then shut off. 11.9 ml methyl isocyanate was added under gentle reflux in 10–12 minutes and refluxed one hour longer. The reaction mixture was evaporated in vacuum and a yield of 39 g of a white solid was obtained. A 2.0066 g sample, titrated with 0.05 N HCl, used 0.05 ml at end point. This shows completeness of reaction, since a negligible amount of amine is left unreacted.

EXAMPLE 4

Preparation of methyl carbamoyl derivative of beta tetradecylamine:

$$C_{12}H_{25}\underset{}{\overset{CH_3}{\overset{|}{C}}}HNHCONHCH_3$$

N-beta tetradecyl-N'-methylurea 46 g (0.19 mole) of the beta amine in 60 ml methylene chloride was heated to reflux on a steam bath. 13.7 ml methyl isocyanate in 15 ml methylene chloride was added dropwise, maintaining a gentle reflux, over a period of 10 minutes. The reaction mixture was refluxed one additional hour and then evaporated in vacuum, yielding 53.8 g white solid.

EXAMPLE 5

Preparation of methyl carbamoyl derivative of beta hexadecylamine:

$$C_{14}H_{29}\overset{CH_3}{\overset{|}{C}}HNHCONHCH_3$$

N-beta hexadecyl-N'-methylurea 38.6 g (0.135 mole) beta-hexadecylamine in 60 ml methylene chloride was reacted with 9.6 ml methyl isocyanate in 15 ml methylene chloride in accordance with the procedure in Example 4, yielding a white solid reaction product.

Other N,N' substituted urea antistatic agents in accordance with instant invention can be prepared by using other alkyl isocyanates such as ethyl, propyl, butyl, pentyl and hexyl isocyanate. Similarly, other long chain aliphatic primary amines wherein the amino functional group is attached to any inner carbon atom may be used in the preparation of instant dialkyl urea antistatic and softening agents, such as octyl, nonyl, decyl, heptadecyl, octadecyl, nonadecyl eicosanyl, amine, etc. and mixtures thereof. Primary amines where the amino group is attached to the terminal carbons, such as dodecylamine, hexadecylamine, octadecylamine, cocoamine and the like yield dialkyl ureas with very limited effect on static and fabric softening.

Accordingly, it has been found that the substituents on the nitrogen atoms of the urea effective as softening and antistatic agents are one short alkyl chain containing 1–6 carbons, and one secondary long aliphatic chain containing 8–22 carbons, one on each nitrogen.

The antistatic compounds of this invention may be used in conjunction with detergents which include anionic detergents such as alkylbenzene-sulfonic acid and its salts, e.g. compounds of the formula alkyl-phenyl-$SO_3$-M, wherein alkyl is an alkyl radical of $C_8$ to $C_{22}$ and preferably $C_{10}$ to $C_{18}$ and M is hydrogen or an alkali metal, which compounds comprise a well-known class of anionic detergents and include sodium dodecylbenzene sulfonate, potassium dodecylbenzenesulfonate, sodium laurylbenzenesulfonate, sodium cetylbenzenesulfonate. Others include paraffin sulfonates, alkyl sulfates, alcohol ether sulfates, olefin sulfonates and the alkylphenolethoxylate sulfates (e.g., sodium dinonylphenoxynonaethoxyethanol sulfate, sodium dodecylhexadecaethoxyethanol sulfate), and other equivalent water-soluble salts, particularly of the alkali metal series.

Among the above-noted alkylbenzene-sulfonic acid and salts thereof, the preferred compounds include those which are biodegradable and which are particularly characterized by a linear alkyl substituent of from $C_{10}$ to $C_{22}$ and preferably from $C_{12}$ to $C_{15}$. It is, of course, understood that the carbon chain length represents, in general, an average chain length since the method for producing such products usually employs alkylating reagents of mixed chain length. It is clear, however, that substantially pure olefins as well as alkylating compounds used in other techniques can and do give alkylated benzene sulfonates wherein the alkyl moiety is substantially (i.e., at least 99%) of one chain length, i.e., $C_{12}$, $C_{13}$, $C_{14}$, or $C_{15}$. The linear alkyl benzene sulfonates are further characterized by the position of the benzene ring in the linear alkyl chain with any of the position isomers (i.e., alpha to omega) being operable and contemplated.

In addition to the benzene sulfonates one may also employ the lower alkyl ($C_1$ to $C_4$) analogs of benzene such as toluene, xylene, the trimethyl benzenes, ethyl benzene, isopropyl benzene and the like. The sulfonates are generally employed in the water soluble salt form which include as the cation, the alkali metals, ammonium and lower amine, and alkanolamine cations.

Examples of suitable linear alkyl benzene sulfonates include:

sodium n-decyl benzene sulfonate
sodium n-dodecyl benzene sulfonate
sodium n-tetradecyl benzene sulfonate
sodium n-pentadecyl benzene sulfonate
sodium n-hexadecyl benzene sulfonate and the corresponding lower alkyl substituted homologues of benzene as well as the salts of the cations previously referred to. Mixtures of these sulfonates may, of course, also be used with mixtures which may include compounds wherein the linear alkyl chain is smaller or larger than indicated herein provided that the average chain length in the mixture conforms to the specific requirements of $C_{10}$ to $C_{22}$.

The linear paraffin sulfonates are also a well-known group of compounds and include water-soluble salts (alkali metal, amine, alkanolamine, and ammonium) of:

1-decane sulfonic acid
1-dodecane sulfonic acid
1-tridecane sulfonic acid
1-tetradecane sulfonic acid
1-pentadecane sulfonic acid
1-hexadecane sulfonic acid as well as the other position isomers of the sulfonic acid group.

In addition to the paraffin sulfonates illustrated above, others with the general range of $C_{10}$ to $C_{22}$ alkyls may be used, with the most preferable range being from $C_{12}$ to $C_{20}$.

The linear alkyl sulfates which are contemplated in this invention comprise the range of $C_{10}$ to $C_{20}$. Specific examples include sodium n-decyl sulfate; sodium n-dodecyl sulfate; sodium n-hexadecyl sulfate; sodium n-heptadecyl sulfate; sodium n-octadecyl sulfate; and the ethoxylated (1 to 100 moles ethylene oxide) derivatives; and, of course, the other water-soluble salt-forming cations mentioned above.

Included in the group of anionic detergents, which have been described above as suitable in the present invention, are the olefin sulfates, including long chain alkene sulfonates, long chain hydroxyalkane sulfonates, as well as disulfonates. Examples of suitable olefin sulfonates, which are merely illustrative of the general class, are sodium dodecenyl-1 sulfonate, sodium tetradecenyl-1 sulfonate, sodium hexadecenyl-1 sulfonate, and sodium octadecenyl-1 sulfonate.

Also useful in conjunction with instant antistatic and softening dialkyl ureas are non-ionic detergents which are commercially known, such as alkylaryl polyglycol detergents such as alkylphenol-alkylene oxide and preferably ethylene oxide condensates (2–200 moles ethylene oxide), e.g., p-isooctyl phenolpolyethylene oxide (10 ethylene oxide units), long chain alcohol-ethylene oxide condensation products (2–200 moles ethylene oxide), e.g., dodecyl alcohol-polyethylene oxides having 4–16 ethylene oxide units per molecule, polyglycerol monolaurate, glycol dioleate, sorbitan monolaurate, sorbitan monostearate, sorbitan monopalmitate, sorbitan monooleate, sorbitan sesquioleate, the condensation products of ethylene oxide with sorbitan esters of long chain fatty acids (Tweens), alkylolamides, amine oxides, phosphine oxides, etc..

In addition to the anionic and nonionic detergents which may be employed in conjunction with the antistatic agents of instant invention, cationic, ampholytic, and zwitterionic compounds have also been found to be useful. Representative of those compounds which may be employed in conjunction with the instant fabric antistatic compounds include quaternary ammonium compounds, e.g., distearyl dimethyl ammonium chloride, cetyl trimethyl ammonium bromide, sodium 3-dodecylamino propionate, fatty carbamides, etc..

The composition of the instant invention may also include, in addition to instant antistatic compounds and conventional anionic, cationic, and nonionic detergents, builders, brighteners, hydrotropes, germicides, soil suspending agents, anti-redisposition agents, antioxidants, bleaches, coloring materials (dyes and pigments), perfumes, water-soluble alcohols, foam boosters, non-detergent alkali metal benzene sulfonates, etc..

The builder is, generally, a water-soluble, inorganic salt which may be a neutral salt, e.g., sodium sulfate or an alkaline builder salt such as phosphates, silicates, bicarbonates, carbonates, citrates and borates. The preferred builders are those characterized as condensed phosphates such as polyphosphates and pyrophosphates and alkali citrates. Specific examples of alkaline salts are: tetrasodium pyrophosphate, pentasodium, tripolyphosphate (either Phase I or Phase II), sodium hexametaphosphate, and the corresponding potassium salts of these compounds, sodium and potassium silicates, e.g., sodium metasilicate and other silicates (e.g., $Na_2O$; 1.6–$3SiO_2$), sodium carbonate, potassium carbonate and sodium and potassium bicarbonate, sodium citrate and potassium citrate. Other salts may also be used wherein the compounds are water-soluble including the general class of alkali metals, alkaline earth metals, amine, alkanolamine, and ammonium salts. Other builders which are salts of organic acids may also be used, and in particular the water-soluble (alkali metal, ammonium substituted ammonium and amine) salts of aminopolycarboxylic acids such as:

ethylene diamine tetra-acetic acid
nitrilo triacetic acid
diethylene triamine pentaacetic acid
N-(2-hydroxyethyl)-ethylene diamine triacetic acid
2-hydroxyethyl-iminodiacetic acid
1,2-diaminocyclohexane diacetic acid and the like. Water-insoluble builders having cation-exchange properties may be used also, such as the sodium aluminosilicates, for example Zeolite A, which may be used alone or in combination with other builders such as sodium tripolyphosphate.

In addition to the above ingredients one may, as previously delineated, employ hydrotropes in connection with the composition of the instant invention. The useful hydrotropes include such compounds as sodium xylene sulfonate, potassium xylene sulfonate, sodium and potassium toluene sulfonates, and the position isomers thereof, ethyl benzene sulfonate, cumene sulfonates, and the like.

In addition to compositions comprising the novel dialkyl urea antistatic and softening agents of the instant invention in combination with detergent and conventional laundering additives, it is noted that said antistatic agents may in addition be formulated in suitable vehicles for addition to the laundering cycle with the concomitant addition of detergent materials. In connection therewith said dialkyl urea may be solubilized and/or dispersed by conventional techniques utilizing alcohols, ether alcohols, hydrotropic solutions, glycols, and the like. Furthermore, it is noted that said antistatic agents may also be absorbed onto suitable salts and/or other carriers for addition to the laundering cycle such as, for example, phosphates, borax, silicates, sodium sulfonate, clays, starch, and the like. A preferred carrier is a carbonate base bead comprising 49.04 parts sodium bicarbonate, 10.67 parts sodium carbonate, 17.00 parts silicate solids, 0.015 parts xylene red color and 6.00 parts water.

The following Example specifically illustrates a method of dispersing the dialkyl ureas on carbonate base beads. However, it is merely illustrative thereof and it is not limited thereto.

EXAMPLE 6

Base Bead Composition

| Ingredients | Parts |
|---|---|
| $NaHCO_3$ | 49.04 |
| $Na_2CO_3$ | 10.67 |
| Silicate Solids | 17.00 |
| Xylene Red Color | 0.015 |
| $H_2O$ | 6.00 |

10 g of warm bead composition which was preheated on a steam bath was added to 5 g melted dialkyl urea of Example 1 on a steam bath and stirred vigorously. The mixture was substantially free flowing.

The amount of dialkyl urea utilized in connection with detergent compositions is generally considered to be a relatively small proportion as compared to the weight of the active ingredients therein. It is noted, however, that one need only employ an effective amount of said dialkyl urea which in fact produces the desired antistatic and softening action on fabrics. It is preferred that said urea be present in an amount of from about 2% to about 25%, and preferably 5% to 20%, of the total ingredients present in the detergent composition on a weight basis.

The composition of the instant invention may be employed in either particulate, liquid, tablet, or any other conventional form. Moreover, as noted above, the novel dialkyl ureas as disclosed herein may be employed as antistatic and softening fabric agents by being applied to textile materials during the washing process, with the concomitant addition of detergent materials thereto, or used as a presoak product prior to washing or as a rinse cycle additive after the wash cycle.

The laundering and presoak composition of instant invention will now be illustrated by the following more detailed examples thereof. It is noted, however, that these compositions are merely illustrative and it is not limited thereto.

EXAMPLES 7a, b, c, d, e

Non-phosphate anionic detergent

| Ingredient | % |
|---|---|
| Sodium Dodecyl benzenesulfonate | 23 |
| Sodium carbonate | 20 |
| Sodium silicate (1:2.4) | 15 |
| Soap (Sodium Coco-Tallow 80:20) | 2 |
| Nonionic detergent* | 1 |
| Borax | 3 |
| Sodium carboxymethylcellulose | 1 |
| Optical Brightener | .5 |
| Calcined aluminum silicate | 1 |
| Sodium sulfate | 30.5 |
| Water | 3 |
| | 100.0 |

*Fatty alcohol ($C_{12-15}$) with average of 7 moles ethylene oxide.

This composition is spray-dried to produce a powder. To 100 g of this formulation is added 2-10 g dialkyl urea antistatic and softening agent:

a. N-beta dodecyl-N'-methylurea b. Ethyl carbamoyl derivative of Armeen L-15 c. $CH_3(CH_2)_{8-11}CHNHCONHCH_3$ (Methyl carbamoyl derivative
|
$CH_3$ of Armeen L-11)

d. $CH_3(CH_2)_{12-17}CHNHCONHCH_3$ (Methyl carbamoyl deriva-
|
$CH_3$ tive of Armeen L-15)

e. Propyl carbamoyl derivative of Armeen L-15

EXAMPLE 8a, b, c, d, e

Phosphate-built Anionic Detergent

| Ingredient | % |
|---|---|
| Sodium Tridecyl benzenesulfonate | 15 |
| Nonionic detergent* | .5 |
| Sodium silicate (1:2.4) | 10.5 |
| Sodium tripolyphosphate | 33 |
| Sodium carbonate | 5 |
| Sodium sulfate | 24 |
| Sodium Carboxymethylcellulose | .25 |
| Optical Brighteners | .5 |
| Borax | 1.0 |
| Perfume | .15 |
| Water | 10.1 |
| | 100.0 |

*Fatty alcohol ($C_{12-15}$) condensed with average of 7 moles ethylene oxide.

This composition is also spray-dried to produce a powder.

To this composition is added 2-10 g of the dialkyl urea antistatic and softening agent:

a. methyl carbamoyl derivative of beta-tetradecylamine of Example 4.

b. methyl carbamoyl derivative of beta-hexadecylamine of Example 5.

c. $CH_3(CH_2)_{8-11}CHNHCONHCH_3$
|
$CH_3$ d. $CH_3(CH_2)_{12-17}CHNHCONHCH_3$
|
$CH_3$ e. ethyl carbamoyl derivative of Armeen L-15.

EXAMPLE 9 a, b, c, d, e

Built Nonionic Detergent

| Ingredient | % |
|---|---|
| Ethoxylated alcohol* | 19 |
| Sodium tripolyphosphate | 60 |
| Sodium silicate (1:2.4) | 10 |
| Optical Brighteners | 2 |
| Enzyme (Proteolytic) | 1.5 |
| Perfume and Color | 0.35 |
| Moisture | 7.15 |
| | 100.0 |

*Fatty alcohol ($C_{12-13}$) condensed with an average of 6.5 moles ethylene oxide.

To 40 g of this formulation which is in the form of a powder, is added 2-10 g of fabric antistatic softening agent:

a. N-($C_{18}$ secondary linear hydrocarbon)-N'-methylurea b. N-($C_{20}$ secondary linear hydrocarbon)-N'-methylurea c. $CH_3(CH_2)_{8-11}CHNHCONHCH_3$
|
$CH_3$ d. $CH_3(CH_2)_{12-17}CHNHCONHCH_3$
|
$CH_3$ e. $(C_5H_{11})_2CHNHCONHCH_3$

EXAMPLE 10

Presoak Product

| Ingredient | Parts |
|---|---|
| Sodium Linear tridecylbenzene sulfonate | 6.3 |
| Sodium silicate | 8.3 |
| Sodium tripolyphosphate | 41.7 |
| Sodium sulfate | 35.4 |
| Water | 8.3 |

6 g of the dialkyl urea of Example 1 and 48 g of the above presoak formulation were added to a GE washer at 120° F. and agitated to dissolve. Swatches of 4 fabrics, cotton terry, dacron, nylon and dacron/cotton were added, agitated for 1 minute and let soak overnight. In the morning, the water was spun out and 100 g of a phosphate-built anionic detergent was run through the regular wash cycle at 120° F. Another run was made with the same dialkyl urea, the detergent and the presoak formulation added at the same time to the washer, and a control was run with the detergent and presoak product alone. The results given in Table I, clearly show the antistatic and softening activity of instant ureas in presoak formulation as well as in detergent compositions.

TABLE I

| Material | Static (1) | Softness (2) |
|---|---|---|
| Example 1 urea, presoak | 0.1 kV | 6 |
| Example 1 urea, no presoak | 0 | 8 |
| Control | 22 | 1 |

(1) Sum of the absolute values of surface charges of the 4 fabrics on removal from the dryer.
(2) Subjective reading on a scale of 1 to 10; higher values are softer.

The presence of the methyl carbamoyl derivative of Armeen L-15 boosted detergency of the composition and showed insignificant yellowing and brightener effects.

Utility of the dialkyl ureas in reducing static electricity and enhancing softness properties of fabrics during the laundering process, without yellowing or depressing brightening was shown in a test run in GE washers (18 gal. water) at 120° F. with a mixed clean fabric load (cotton terry, dacron double knit, Banlon nylon, dacron/cotton 65/35) and soiled swatches (Test Fabrics nylon, Test Fabrics cotton, Scientific Services clay on cotton, Scientific Services clay on dacron/cotton, EMPA cloth), and tumble dried for 45 minutes. In each case 5 g of the test material was added to the washer simultaneously with 40 g of the formulation of Example 9 or as indicated.

TABLE II

| | Amide | Static Value | Softness |
|---|---|---|---|
| 1. | None | 13.7 kV | 1 |
| 2. | L-15 methyl urea | 0 | 8 |
| 3. | L-15 ethyl urea | 0 | 5 |
| 4. | L-15 propyl urea | 0.1 | 6 |
| 5. | + 10 g base beads of Example 6 | 5.6 | 1 |
| 6. | 5 g L-15 methyl urea* | 0.2 | 8 |
| 7. | 5 g beta $C_{12}$ methyl urea* | 0.2 | 6 |
| 8. | 5 g beta $C_{14}$ methyl urea* | 0.7 | 6 |
| 9. | 5 g beta $C_{16}$ methyl urea* | 5.0 | 4 |
| 10. | 5 g beta $C_{18}$ methyl urea* | 5.8 | 5 |
| 11. | 5 g beta $C_{20}$methyl urea* | 5.6 | 5 |
| 12. | 5 g beta $C_{22}$ methyl urea* | 5.5 | 4 |

*The dialkyl urea is dispersed in 10 g base beads as shown in Example 6.

Using concentrations from 7.5 to 240 ppm, the compounds of this invention were found to have no significant effect on overall detergency of the soiled swatches, to cause no loss in brightener efficiency, and to cause no significant yellowing of nylon or cotton in contrast to quaternary ammonium compounds similarly tested which were deficient in all these areas. The reduction in static electricity on the tumble dried fabrics was found to be concentration dependent with over 90% effectiveness at levels of 60 ppm or more in contrast to an average redcuction of 30% for a quaternary ammonium antistatic agent which did not improve with increasing concentration.

Comparative results with dialkyl ureas wherein the long chain substituent on the nitrogen is a primary hydrocarbon radical, not embraced by instant invention, show their inability to soften fabrics and reduce static electricity generated during the washing and drying of mixed fabric loads.

The efficiency of the methyl carbamoyl derivative of Armeen L-15 (L-15 methyl urea) in comparison with the derivative of cocoamine (coco methyl urea) is shown by tests conducted in GE washers (18 gal water) at 120° F. with a mixed clean fabric load of cotton/polyester terry, dacron doubleknit, Banlon nylon and 65% dacron/cotton, wherein the test material was added simultaniously with 40 g of the phosphate-built non-ionic detergent of Example 9.

TABLE III

| Amount | L-15 methyl urea | | coco methyl urea | |
|---|---|---|---|---|
| per wash (g) | Static | Softness | Static | Softness |
| 0 | 24.3 | 1 | 24.3 | 1 |
| 0.5 | 15.5 | 1 | 15.6 | 3 |
| 1 | 6.8 | 3 | 20.6 | 1 |
| 2 | 0.5 | 6 | 19.6 | 5 |
| 4 | 0.8 | 9 | 20.6 | 3 |
| 6 | 0.1 | 10 | 10.5 | 4 |
| 8 | 0.05 | 10 | 9.1 | 4 |
| 12 | 0.0 | 10 | 7.4 | 3 |

This table clearly shows that the carbamoyl derivatives of a terminally substituted long chain amine is relatively ineffective as an antistatic and softening agent.

Table IV utilizes 5 g of dialkyl urea with 100 g of the anionic detergents both phosphate-containing and no phosphate-containing as shown in Examples 8 and 7 respectively or as otherwise indicated.

TABLE IV

| Detergent composition | Urea | Softness | Station value |
|---|---|---|---|
| 1. Example 8 | — | 1 | 23.0 |
| 2. Example 8 | L-15 methyl urea | 8 | 0.1 |
| 3. Example 7 | — | 1 | 15.5 |
| 4. Example 7 | L-15 methyl urea | 6 | 0 |
| 5. Example 7 (90g) | $C_9H_{19}CH(CH_3)-NHCONHCH_3$* | 1 | 0.3 |
| 6. Example 9 (40g) + 15g base beads of Example 6 | — | 1 | 27.0 |
| 7. Example 9 | L-15 methyl urea* | 6 | 0 |
| 8. Example 8 + 15g beads of Example 6 | — | 1 | 21.0 |
| 9. Example 8 | L-15 methyl urea* | 8 | 0.15 |
| 10. Example 7 + 15g base beads of Example 6 | — | 1 | 16.8 |
| 11. Example 7 | L-15 methyl urea* | 10 | 0 |
| 12. Example 7 (90g) | L-11 methyl urea* | 5 | 0.05 |
| 13. Example 7 (90g) | L-11 methyl urea + L-15 methyl urea (1:1)* | 8 | 0 |

*5g dispersed in 10g base beads of Example 6.

The ability of a dialkyl urea with a secondary long alkyl chain substituent to reduce static electricity and provide fabric softening in the presence of both anionic and non-ionic detergents, either phosphate-built or non phosphate-containing is clearly shown in the above Examples.

The addition of bleach during the wash cycle does not adversely affect the static suppression properties and the softening properties of the ureas of instant invention, nor is there any interference by these antistatic and softening agents with the bleaching action.

In connection with the subject compositions, it is noted that in built detergents, the organic cleaning agent, i.e., the anionic, nonionic, etc., compound may comprise from about 5% to upwards of 75% by weight of the total formulation and usually varies from 5% to 35% by weight. In liquid compositions, the amount of water used is relatively high in order to obtain pourable and generally stable systems. In these, total solids may vary from a few percent, i.e., 2–10%, upwards of about 50–60% with the organic detergent present, usually in amounts from about 2–25% and preferably 5–15%. In solid formulation, i.e., powder, etc., total solids may run as high as 90% or more and here the organic detergent may be used at the high concentrations above indicated, but usually the range is 5-25%. The second major component of the built or heavy duty liquids, and this is true of the solid (i.e., powdered or tableted types) formulations also, is the alkaline builder salt, and the amount thereof again may vary considerably, e.g., from 5-75% of the total composition. In solid formulations, larger percentages are generally employed, e.g., 15-50%, whereas in the liquid types, the salts are used in lesser amounts, e.g., 5-25% by weight of the total composition.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. Dialkyl urea antistatic and softening agents substituted on both nitrogen atoms and having the formula:

$$RNHCONHR'$$

wherein R is a short alkyl group of 1-6 carbons, and R' is a secondary aliphatic hydrocarbon chain of 8-22 carbons.

2. A compound in accordance with claim 1, which is a methyl carbamoyl derivative of a long chain aliphatic amine, wherein the amino nitrogen is attached to a non-terminal methylene group.

3. A compound in accordance with claim 2, which has the formula:

$$CH_3(CH_2)_{12-17}\underset{\displaystyle CH_3}{\underset{|}{C}}HNHCONHCH_3.$$

4. A compound in accordance with claim 1, which has the formula:

$$CH_3(CH_2)_{12-17}\underset{\displaystyle CH_3}{\underset{|}{C}}HNHCONHCH_2CH_3$$

5. A compound in accordance with claim 2, which is a methyl carbamoyl derivative of beta dodecylamine.

6. A compound in accordance with claim 2, which has the formula:

$$CH_3(CH_2)_{8-11}\underset{\displaystyle CH_3}{\underset{|}{C}}HNHCONHCH_3$$

7. A non-yellowing antistatic and softening composition for laundering fabrics comprising an effective antistatic and softening amount of the dialkyl urea antistatic and softening agent defined in claim 1, and a detergent selected from the group consisting of anionic, nonionic, cationic, ampholytic and zwitterionic detergent materials.

8. A non-yellowing antistatic composition for laundering fabrics comprising about 2-25% by weight of the dialkyl urea antistatic and softening agent defined in claim 1, and a nonionic detergent.

9. The composition of claim 8, additionally comprising optical brighteners and builders.

10. The composition of claim 7, wherein the detergent is anionic and the antistatic agent constitutes about 2-25% by weight of the composition.

11. The composition of claim 10, additionally comprising optical brighteners and builders.

12. The composition of claim 7, wherein the urea antistatic and softening agent is absorbed on a carbonate base bead carrier comprising sodium bicarbonate, sodium carbonate and silicate solids.

13. A method of protecting fabrics against acquiring static electricity and simultaneously imparting softness thereto during the laundering process comprising contacting fabrics with the composition of claim 7.

14. A process of imparting both antistatic and softening properties to fabrics which consists in treating fabrics with a composition containing an antistatic and softening amount of the compound defined in claim 1.

15. The method of protecting fabrics against acquiring static electricity and simultaneously imparting softness thereto, which consists in laundering the fabrics in a composition comprising a detergent and the anti-static and softening compound defined in claim 1.

16. The method of claim 14, wherein the antistatic and softening agent is added during the rinse cycle after the wash cycle.

17. The method of claim 14, wherein the antistatic and softening agent is added to a presoak composition prior to the wash cycle.

18. The method of claim 14, wherein the antistatic and softening agent is added during the wash cycle.

* * * * *